US00PP20207P2

(12) United States Plant Patent
Berry

(10) Patent No.: US PP20,207 P2
(45) Date of Patent: Aug. 4, 2009

(54) ***LIRIOPE* PLANT NAMED 'MARANT'**

(50) Latin Name: *Liriope muscari*
Varietal Denomination: Marant

(75) Inventor: James Bryan Berry, Daphne, AL (US)

(73) Assignee: Plant Development Services, Inc., Loxley, AL (US)

( * ) Notice: Subject to any disclaimer, the term of this patent is extended or adjusted under 35 U.S.C. 154(b) by 154 days.

(21) Appl. No.: 11/297,141

(22) Filed: Dec. 8, 2005

(51) Int. Cl.
*A01H 5/00* (2006.01)

(52) U.S. Cl. ..... Plt./450
(58) Field of Classification Search ..... Plt./450, Plt./263
See application file for complete search history.

(56) References Cited

PUBLICATIONS

The Southern Living Garden Book, Oxmoor House, Inc. 2004, p. 395.*

Dayton Nurseries, Lilyturf Liriope [online], [retrieved on Jan. 31, 2007]. Retrieved from the Internet <http://www.daytonnursery.com/Encyclopedia/Perennials/Liriope.htm> 4 pages.*

* cited by examiner

*Primary Examiner*—June Hwu
(74) *Attorney, Agent, or Firm*—Breiner & Breiner, LLC

(57) ABSTRACT

A new and distinct variety of *Liriope* that possesses unique color and leaf width.

1 Drawing Sheet

Latin name: *Liriope muscari.*
Variety denomination: 'Marant'.

BACKGROUND OF THE INVENTION

James Berry identified the plant as a unique variegated seedling from an unknown parentage in a commercial nursery in March 1993 in Loxley, Ala. The plant was part of 100,000 individual plants purchased from a North Carolina nursery. In the population, 15 plants were unusual and unique. This invention was one of those plants.

Asexual propagation of the new plant by division bas been under Mr. Berry's direction at the same location. The new plant retains its distinctive characteristics and reproduces true to type in successive generations. The plant cannot be reproduced true from seed.

SUMMARY OF THE INVENTION

1. Marginal variegation of the leaf blade is yellow in early growth stages.
2. Marginal variegation of the leaf blade is white in mature growth stages.
3. The above traits yield tri color foliage of yellow, white, and green.
4. Leaf blade is wider than traditional variegated *Liriope.*
5. Easily propagated by division.
6. Heat and drought resistant.
7. Good groundcover.
8. Tolerates full sun to shade.
9. Desirable in planters.
10. Effective in mass.
11. Withstands wind and salt spray.
12. An excellent plant for borders.
13. Hardy to Zone 7.

BRIEF DESCRIPTION OF ILLUSTRATION

Figure 1:
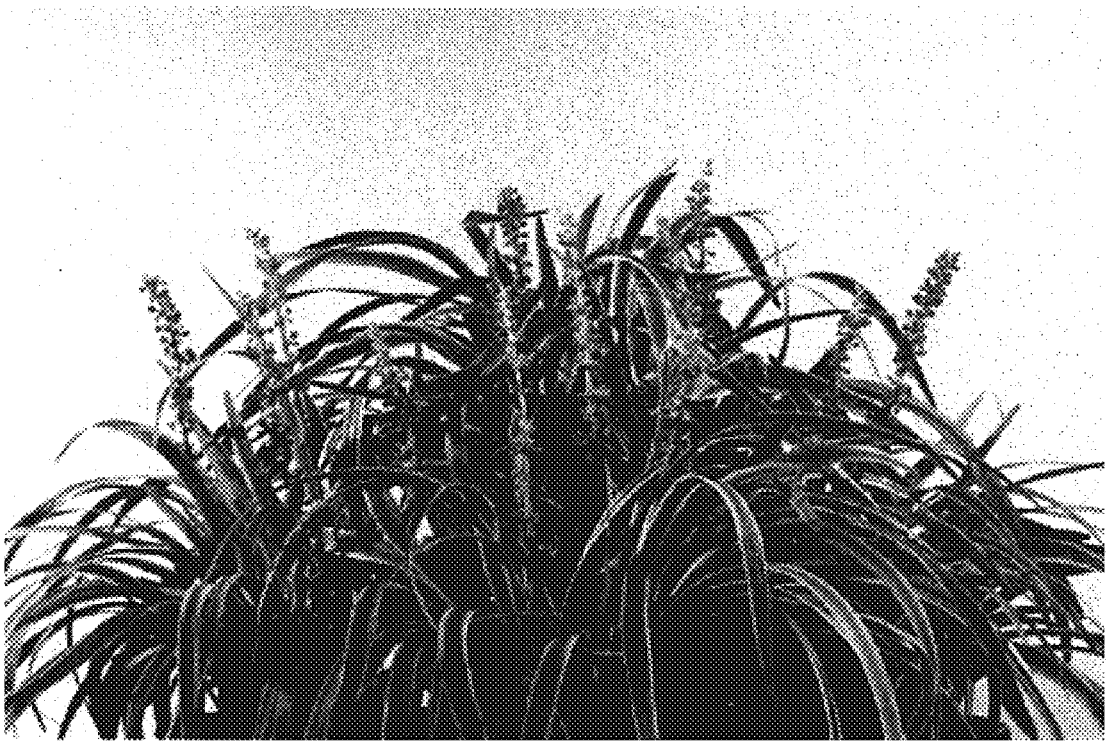

FIG. 1—Demonstrates clumping growth habit and profusion flowering character.

Figure 2:
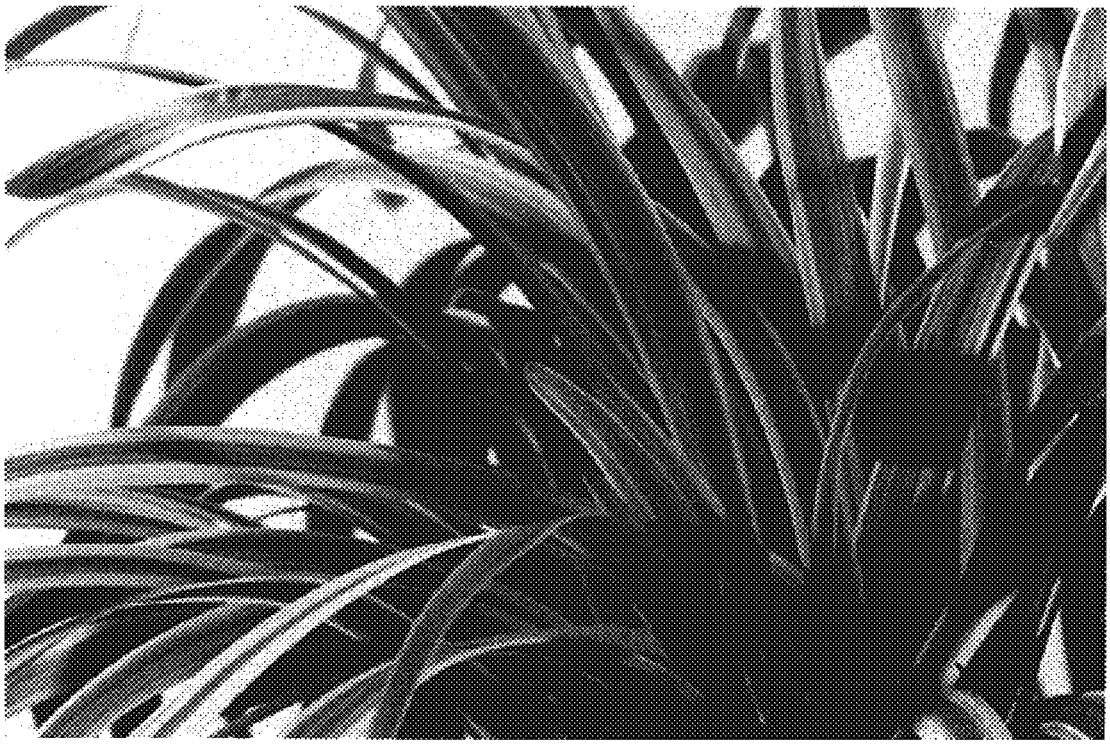

FIG. 2—Shows the unique foliage colors. The yellow and green blades are immature, recent growth. The white and green blades arm more mature.

DETAILED BOTANICAL DESCRIPTION OF THE PLANT

The plant has a clumping growth habit. The leaf blades are slightly wider than other variegated cultivars of *Liriope muscari.* The green portion of the blade is darker green and slightly wider that other variegated cultivars of *Liriope muscari.* The flowering characteristics are similar to other cultivars of *Liriope muscari.* Comparison with parent—Parent plant not observed. The variegation of the leaf blade margins is yellow until the blade is mature. The margins mature to white. This visual effect is different depending on the growth cycle of the cultivar.

Average spread and height: 12"×21–24". Color (RHS Color Chart).
Leaf surface upper & lower (mature): Yellow-Green 147A, Yellow-Green 147B, Yellow-Green 144A, Yellow-Green 151A & Yellow-White 157A.
Leaf surface upper (immature): Yellow-Green 144A & Yellow-Green 145C.
Leaf surface lower (immature): Yellow-Green 144B & Yellow-Green 145D.
Leaf veins: Yellow-Green 145A.
Flower bud (mature): Violet-Blue 92B & Violet-Blue 92C.
Flower bud (immature): Violet- Blue 92C.
Flower petal: Violet-Blue 92A.
Peduncle (apex): Purple 78B & Purple 78D.

Peduncle (middle): Yellow-Green 152D.
Peduncle (base): Purple 77A.
Fruit — Not observed at this time.
Leaf shape: Linear, arching, coriaceous, basal leaf arrangement.
Leaf average size:
*Length.*—16⅜".
*Width.*—7/16".
Leaf surface texture (upper): Short stiff hairs (puberulent) along veins; slightly semi-glossy.
Leaf surface texture (lower): Glaucous, matte.
Leaf apex shape: Subobtuse.
Leaf margin: Entire with slight puberulence.
Inflorescence form: Terminal Raceme.
Average inflorescence size: 10–14".
Flower fragrance: Slight fragrance.
Floret size: 3/16".
Peduncle length: 10–14".
Peduncle surface texture: Glabrous, smooth, ridged & furrowed.
Fruit: —not observed at this time.

It is claimed:

1. A new and distinct variety of *Liriope* plant named 'Marant' illustrated and described.

* * * * *